United States Patent [19]

De Baere

[11] Patent Number: 5,264,349
[45] Date of Patent: Nov. 23, 1993

[54] METHOD AND DEVICE FOR DETERMINING IN AN ACCELERATED MANNER THE ANAEROBIC BIODEGRADABILITY OF A PRODUCT

[75] Inventor: Luc A. De Baere, De Pinte, Belgium

[73] Assignee: Organic Waste Systems, naamloze vennootschap, Antwerp, Belgium

[21] Appl. No.: 687,700

[22] Filed: Apr. 19, 1991

[30] Foreign Application Priority Data

Feb. 1, 1991 [BE] Belgium .............................. 9100096

[51] Int. Cl.$^5$ .............................................. C12Q 1/02
[52] U.S. Cl. ....................................... 435/29; 210/603; 210/613; 435/167; 435/170; 435/262; 435/807
[58] Field of Search ................. 435/170, 29, 807, 167, 435/262; 210/603, 613

[56] References Cited

U.S. PATENT DOCUMENTS

| | | | |
|---|---|---|---|
| 4,062,770 | 12/1977 | Kneer | 210/12 |
| 4,684,468 | 8/1987 | De Baere | 210/603 |

FOREIGN PATENT DOCUMENTS

| | | |
|---|---|---|
| 0131319 | 1/1985 | European Pat. Off. . |
| 0205721 | 12/1986 | European Pat. Off. . |
| 3214798 | 4/1982 | Fed. Rep. of Germany . |
| 3438057 | 10/1984 | Fed. Rep. of Germany . |
| 517845 | 8/1974 | Japan . |

OTHER PUBLICATIONS

Nakasaki, et al, "Change In Microbial Numbers During Thermophilic Composting Of Sewage Sludge With Reference To $CO_2$ Evolution Rate", *App. and Envir. Microbio.*, 49(1):37–41 (1985).

*Primary Examiner*—Herbert J. Lilling
*Attorney, Agent, or Firm*—Foley & Lardner

[57] ABSTRACT

Method for determining in an accelerated manner the biodegradability of at least one product under anaerobic conditions which are similar to those in a dump, characterized in that a mixture with a dry substance content of between 25 and 50% is prepared with more than 80 weight-% of an active anaerobic inoculum and less than 20 weight-% of the product, on the one hand, at least one quantity of this mixture and, on the other hand, at least one quantity of the inoculum is subjected in the same manner to a fermentation at a temperature of between 30 and 60 degrees Centigrade in anaerobic conditions, the amount of biogas that is released with both these fermentations is separately measured or calculated, starting with these amounts the amount of biogas produced by the product alone is deduced and starting with the latter amount the degradability of the product itself is determined, this is the amount of carbon which was degraded from the product and converted into $CO_2$ and $CH_4$.

19 Claims, 4 Drawing Sheets

METHOD AND DEVICE FOR DETERMINING IN AN ACCELERATED MANNER THE ANAEROBIC BIODEGRADABILITY OF A PRODUCT

The invention relates to a method for determining in an accelerated manner the biodegradability of at least one product under anaerobic conditions which are similar to those accelerated dump.

The most usual manner for processing organic refuse of industrial and household nature is by means of a sanitary dump. In view of the strict environmental standards which dumping grounds must satisfy the producers of all types of consumer products, packaging materials, etc. strive to bring environmentally friendly and biodegradable products onto the market. It is therefore important to be able to verify how a product will react in a dump and to what degree and in what time period it will be biodegraded.

In a dump anaerobic rotting or fermentation takes place which arises spontaneously when the dumped material is covered with earth for example and the remaining air in the landfill is consumed by the micro-organisms present.

During the consumption of the air present, which takes a few days or weeks, a heating up can be determined of up to 60 degrees Centigrade. After this short aerobic phase the further degradation of the dumped material will take place in the dump under anaerobic conditions.

The moisture content in a dump is strongly dependent upon the refuse which was dumped there and upon the possible rain which seeps into the landfill through the covering layer. Abundant rain or the dumping of drainage sludge from water purification installations can ensure a relatively high moisture in the landfill, although it is estimated that anaerobic fermentation in a landfill will take place with at least 30% dry material. Apart from that in many countries no waste substances are accepted for dumping which contain more than 70% moisture since these substances can usually no longer be called consistent.

Methods are known for determining the biodegradability of the products but these methods are especially directed towards determining this degradability under wet conditions, such as in a water purification installation. These methods are therefore based on wet anaerobic tests whereby a sludge fermentation is performed with the product to be measured. Other methods make use of wet anaerobic tests.

Since the micro-organisms, the temperature and other factors differ considerably in wet conditions from the micro-organisms, the temperature and other factors in the relatively dry conditions of a landfill these known methods are not suitable for accurately determining the degradability of products in a landfill. Apart from that the degradation in a landfill is considerably slower than example in a water purification installation. It can, for example take fifty to hundreds of years, so that methods without acceleration of the degradation are not suitable for determining biodegradability of products in a landfill.

The purpose of the invention is to provide a method for determining in an accelerated manner and very accurately the biodegradability of products under anaerobic conditions which approach the conditions in a landfill.

A further purpose of the invention is to determine in an accelerated manner the anaerobic biodegradability of a product in a landfill in a reproducible and exact manner, such that the results can provide statistical information of the degree and speed of biodegradation of the product under conditions such as occur in a landfill. An additional purpose is to provide a method which takes place under controlled and accelerated conditions, such that this method can be applied in various laboratories whereby reproducible and exact results are always obtained for the determination of the anaerobic degradation of a well defined product in a landfill.

The above mentioned objectives can be achieved by utilizing the invention according to which a mixture with a dry substance content of between 25 and 50% is prepared with more than 80 weight-% of an active anaerobic inoculum and less than 20 weight-% of the product, on the one hand one quantity of this mixture and, on the other hand, at least one quantity of the inoculum is subjected in the same manner to a fermentation at a temperature of between 30 and 60 degrees Centigrade in anaerobic conditions, the amount of biogas that is released with both these fermentations is separately measured or calculated, starting with these amounts the amount of biogas produced by the product alone is deduced and starting with the latter amount the degradability of the product itself is determined, this is the amount of carbon which was degraded from the product and converted into $CO_2$ and $CH_4$.

The fermentations are preferably performed from 7 to 70 days.

In a particular embodiment of the invention at least two quantities of the inoculum and at least two quantities of the product are subjected to the aforementioned fermentation and the degradability of the product is calculated taking the difference between the average of the amounts of biogas from the inoculum and the average of the amounts of biogas from the product.

Of course the degradability of several products can be determined according to the aforementioned method, whereby these products are mixed with the same inoculum, in which case a similar fermentation or a similar number of fermentations of the inoculum is sufficient for the various products.

The pressure and the temperature of the biogas that is obtained are preferably also measured and the measured volumes are reduced to volumes under standard conditions of pressure and temperature.

In a suitable embodiment of the invention an active inoculum is utilized that has had an average production speed of biogas for at least two weeks and preferably a month of at least 10 ml, and preferably 20 to 30 ml, biogas per gram dry substance and per day.

The inoculum is subsequently preferably left unfed and to postferment for approximately 7 to 14 days before employing it for the determination of the degradability.

Use can be made of an active inoculum that was raised under dry conditions with 20 to 50% dry substance content or of an active inoculum that was raised under wet conditions but was later drained to a dry substance content of between 20 and 50%.

The invention also relates to a device which is especially suitable for the application of the method according to one of the preceding embodiments.

The invention especially relates to a device for determining in an accelerated manner the biodegradability of at least one product under anaerobic conditions which are similar to those in a landfill, of which the characteristic consists in that it comprises at least two reactors, means for bringing these to and maintaining them for a specified time at a similar constant temperature which is higher that the ambient temperature, means for separately measuring or calculating the amounts of biogas produced in these reactors.

The means for measuring or calculating the amounts of biogases can comprise means for separately collecting these amounts of biogas produced in these reactors or can comprise means for measuring the flow rate of these amounts of biogas for a time and means for calculating the amounts of gas from these flow rates and time.

In a particular embodiment of the invention the device includes a gas chromatograph for analyzing the gases.

In a notable embodiment of the invention the device also includes a reactor for inoculum, means for bringing this reactor to and maintaining it for a specified time at this temperature, means for collecting the gases from the reactor and means for measuring their flow rate and amount.

In order to show better the characteristics according to the present invention, some preferred embodiments of a method and device according to the invention are described hereafter, as examples and without any restrictive character with reference to the enclosed drawings in which:

For the determination of the anaerobic biodegradability of a product in a landfill less than 20 weight-% and for example 1 to 20 weight-% and usually 5 to 20 weight-%, calculated on the total mixture, of this product is mixed with more than 80 weight-%, and for example 99 to 80 weight-% or usually 95 to 20 weight-%, of an active anaerobic inoculum, after which this mixture is subjected to a fermentation.

The anaerobic inoculum is raised, starting from household or organic industrial waste or an organic fraction thereof in a graft reactor 1, 2.

The inoculum can be obtained both by wet and by dry fermentation. In the first case the inoculum has a dry substance content of between 20 and 50%, preferably between 35 and 45% in order to approach as closely as possible the real conditions on a dump. A suitable dry anaerobic fermentation is that which is described in U.S. Pat. No. 4,684,468 or U.S. Pat. No. 4,731,170 which are hereby incorporated by reference. With a wet fermentation, this is with a dry substance content of 5 to 10%, after the fermentation the inoculum must be drained to a dry substance content of between 20 and 50% and preferably to between 35 and 45% in order to approach as closely as possible the real conditions in a dump.

Figure 1:
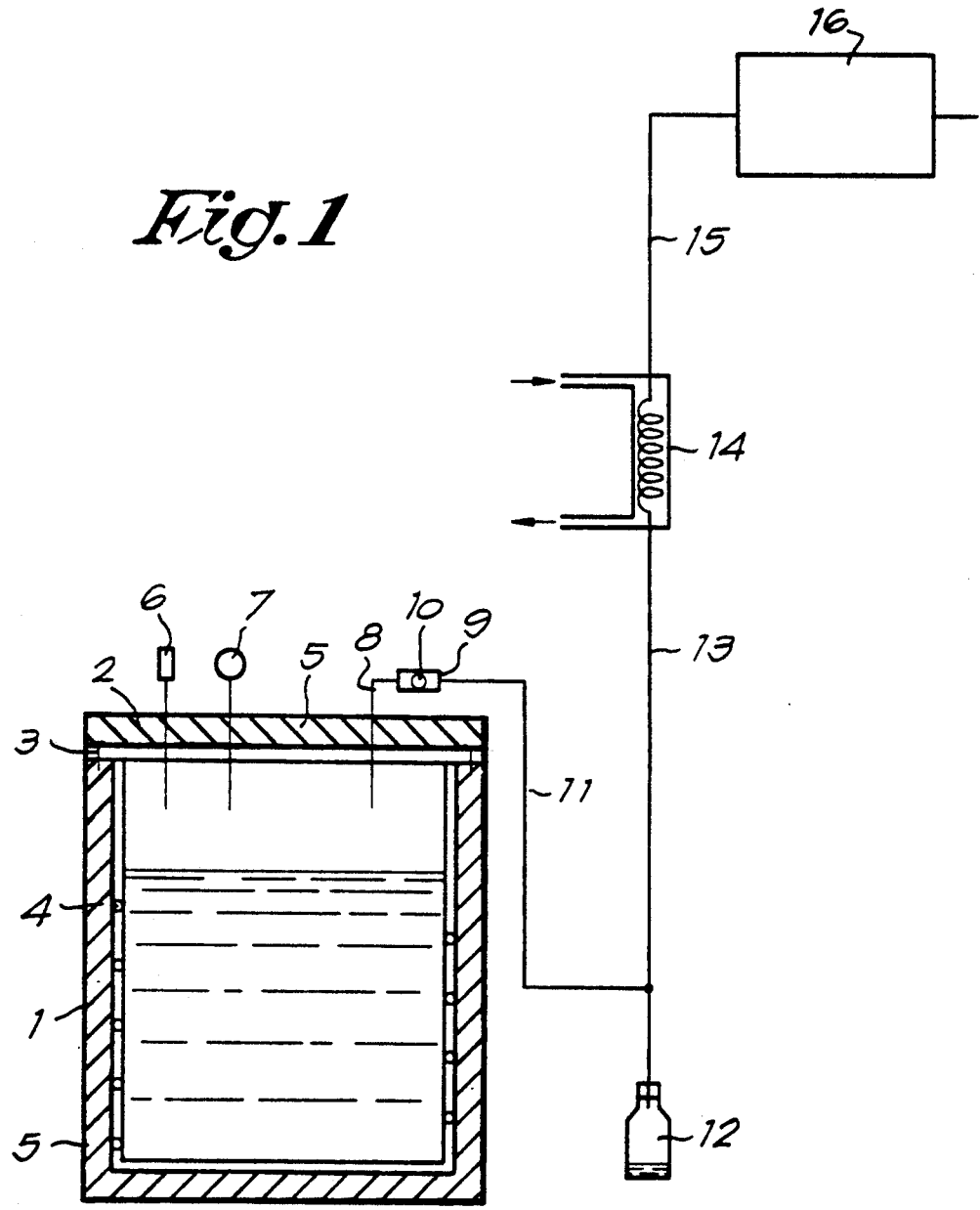
FIG. 1 shows in schematic manner and in cross-section a part of the device according to the invention that is destined for the production of the inoculum.

The raising of the inoculum can in particular be effected with a device as shown in FIG. 1. The graft reactor has been filled with graft from the organic fraction of household refuse with a dry substance content of 20 to 50%. Periodically a quantity of fresh household refuse or an organic fraction thereof must be manually applied to the graft reactor 1, 2, which quantity is mixed with the mass already present. After a good mixing the anaerobic reactor is again closed off from the air with a cover 2 that is hermetically attached by bolts 3. By means of heating tubes or electric tapes 4 the graft reactor 1, 2 is maintained at a temperature of 30 to 60 degrees Centigrade. Both the reactor 1 and the cover 2 are covered with insulation 5 in order to limit the loss of heat. The temperature is monitored with the thermometer 6 and the gas pressure with the manometer 7.

The biogas produced flows through the pipe 8 towards a gas sample flask 9 where gas samples can be taken with the needle through the septum 10. The biogas subsequently flows through the pipe 11 towards a condensation flask 12 where the condensation moisture from the cooled biogas is collected. This biogas is further cooled in a cooling unit 14 to which the gas is supplied through the pipe 13. The dry biogas finally flows through the pipe 15 towards a gas meter 16 where the volume of biogas produced is determined.

The graft reactor 1, 2 is allowed to work for at least four months with a maximum staying time of the inoculum of 30 days under the aforementioned conditions prior to removing inoculum for the determination of the degradability. In the reactor 1, 2 an anaerobic degraded refuse is produced with the necessary living microorganisms. The activity of this refuse that is used as inoculum must be sufficiently great. The graft reactor 1, 2 must have a productivity of at least 10 ml biogas and preferably at least 20 to 30 Nml biogas per gram dry substance in the reactor and per day and this preferably on average for 30 days.

Prior to utilizing the inoculum for the determination of the degradability it is preferably subjected to a short postfermentation, for example for approximately 7 to 14 days, whereby a low biogas production is obtained. During this postfermentation the inoculum is not fed but is allowed to ferment on its own. Because of this it is obtained that during the determination of the biodegradability little degradation will take place in the inoculum utilized and the amount of biogas which is produced by the inoculum itself, will be minimal.

The inoculum preferably has a pH between 7 and 8.5.

The product, of which the anaerobic biodegradability in a dump must be determined, is first accurately weighed and the amount of carbon in this product is calculated according to known methods, for example according to the international standard ISO 625-1975 (F).

Less than 20 weight-%, for example 1 to 20 or 5 to 20 weight-%, of this product is mixed with more than 80 weight-%, for example 99 to 80 or 95 to 80 weight-%, of the aforementioned inoculum. The percentages are calculated on the total amount of the mixture. This product can for example be household refuse, biodegradable plastic etc. The dry substance content of the mixture must lie between 25 and 50% and preferably between 35 and 45%. At the same time a quantity of a reference product with a known biodegradability, such as cellulose, is mixed in the same ratio with the inoculum. The dry substance content of this mixture is also lies between 25 and 50%

One quantity of the inoculum, one quantity of the mixture inoculum-product and one quantity of the mixture inoculum-reference product are in each case placed in different reactors 17 in which an anaerobic fermentation is allowed to take place under similar conditions. The reactors 17 are maintained for seven to seventy and preferably less than sixty days at a temperature of between 30 and 60 degrees Centigrade. In order to obtain an optimum speed a temperature of between 35 and 40 degrees Centigrade or a temperature of between 50 and 55 degrees Centigrade is used.

Figure 2:
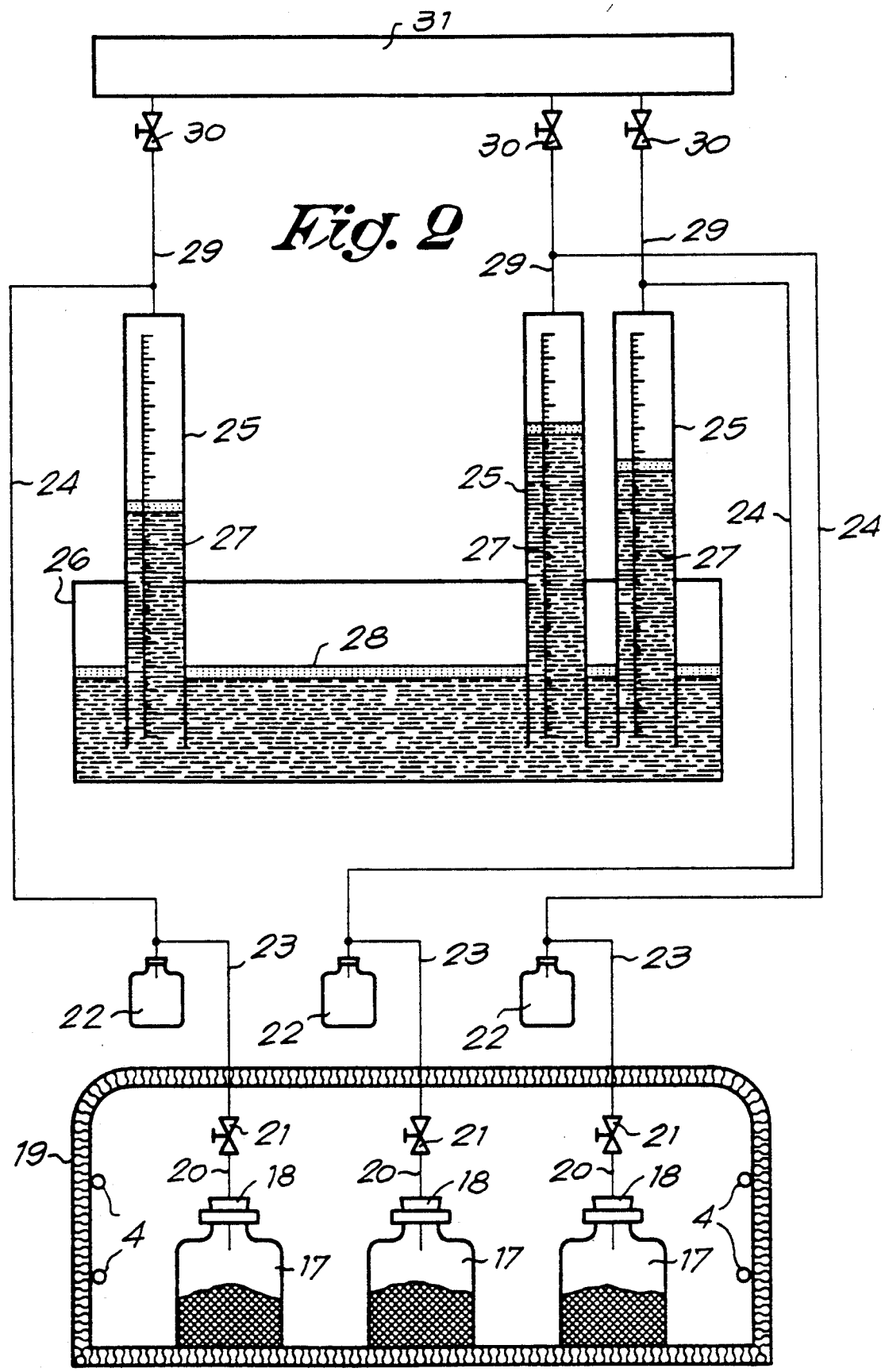
FIG. 2 shows in schematic manner and in cross-section the other part of the device according to the invention in which the actual determination of the biodegradability takes place.

The device shown in FIG. 2 can be utilized. The reactors 17 being glass flasks which are sealed by a rubber stopper 18. The three reactors 17 are together surrounded by an insulating incubator 19. The space inside the incubator 19 is brought up to the aforementioned temperature and maintained at this temperature for the aforementioned time by means of heating elements 4 such as heating tubes or electric tapes.

In each of the reactors 17 produced biogas is collected separately by means of a pipe 20 which extends through the rubber stopper 18 and connects to a valve 21 which is in open position during the gas production. The biogas subsequently flows towards a condensation vessel 22 through the pipe 23 and through the pipe 24 the gas flows further towards a column 25 which is initially filled with acidified water with a pH $<3$. This degree of acidity is established in case of need by adding HCl. The device therefore comprises three columns 25 which are gastight and collect the gas from the reactors 17. With their lower open extremity these columns stand in a tank 26 which is also filled with acidified water 27, which water is covered with a layer of oil 28. This oil must be inert and stable and may not react with the gases produced or the water. The acidified water 27 in the columns 25 is also covered with a layer of oil 28. Because of the biogas the water 27 in the columns will descend in function of the amount of biogas produced. Because of the layer of oil 28 $CO_2$ is prevented from dissolving in the water. The water pressed out of the columns 25 is collected in the tank 26.

Via pipes 29 with valves 30 samples of the biogases produced can be sent to a gas chromatograph 31 in order to be analyzed.

The columns 25, which are empty at the start of a degradability determination, are completely filled with water 27 with a layer of oil 28 thereon by sucking air out of these columns via the pipes 29 and the valves 30 which are brought into open position, while the valves 21 are closed. Thereafter the valves 21 are opened and the valves 30 closed until a gas sample has to be sent to the gas chromatograph 31.

In the above described manner the amount or the volume of biogas produced by the amount of inoculum in one reactor 17 is measured and the amount or the volume of biogas produced by the amount of mixture of inoculum-product in a second reactor 17, from which the amount of biogas produced by the aforementioned product alone can be calculated. If exactly just as much inoculum has been applied in both reactors it is sufficient to deduct just the volume of gas originating from the inoculum from the volume of gas originating from the mixture. From these volumes of biogas the amount of gaseous carbon is calculated which originates from the fermentation of the product itself. It is after all known that the solid carbon in the materials or products in the reactor is transformed during the fermentation into gaseous carbon under the form of $CO_2$ and $CH_4$ whereby one mol of solid carbon gives off one mol of gaseous carbon and this is 22.4 liters of gas at normal temperature and pressure.

The percentage of biodegradability is calculated by dividing the amount of gaseous carbon produced by the product itself by the original amount of carbon in the product and multiplying by 100. By calculating the volume of gas that originates from the reference product itself, of which reference product the biodegradability is known, the method, the device and the adequate activity of the inoculum can be verified. The volume of gas originating from the reference product itself is, in analogue manner as for the product, obtained after deduction of the volume of gas produced by the inoculum present in the mixture of inoculum-reference product of the total volume of gas produced by this mixture.

This calculation is performed at various times during the course of the fermentation in order thus to obtain a development of the degradability in function of time too.

In order to obtain statistically reliable measurement results, preferably at least three quantities of both the pure inoculum and of the mixtures of inoculum-product and inoculum-reference product are subjected to a fermentation in separate reactors 17. Of the three quantities of gas which are obtained from the three quantities of a same mixture or from pure inoculum, and are either directly measured for example with a gas meter, or are calculated working from the flow and the time with a possible periodic measurement of the flow of the gas produced, the average is measured in order to determine further the degradability in the above described manner.

Figure 3:
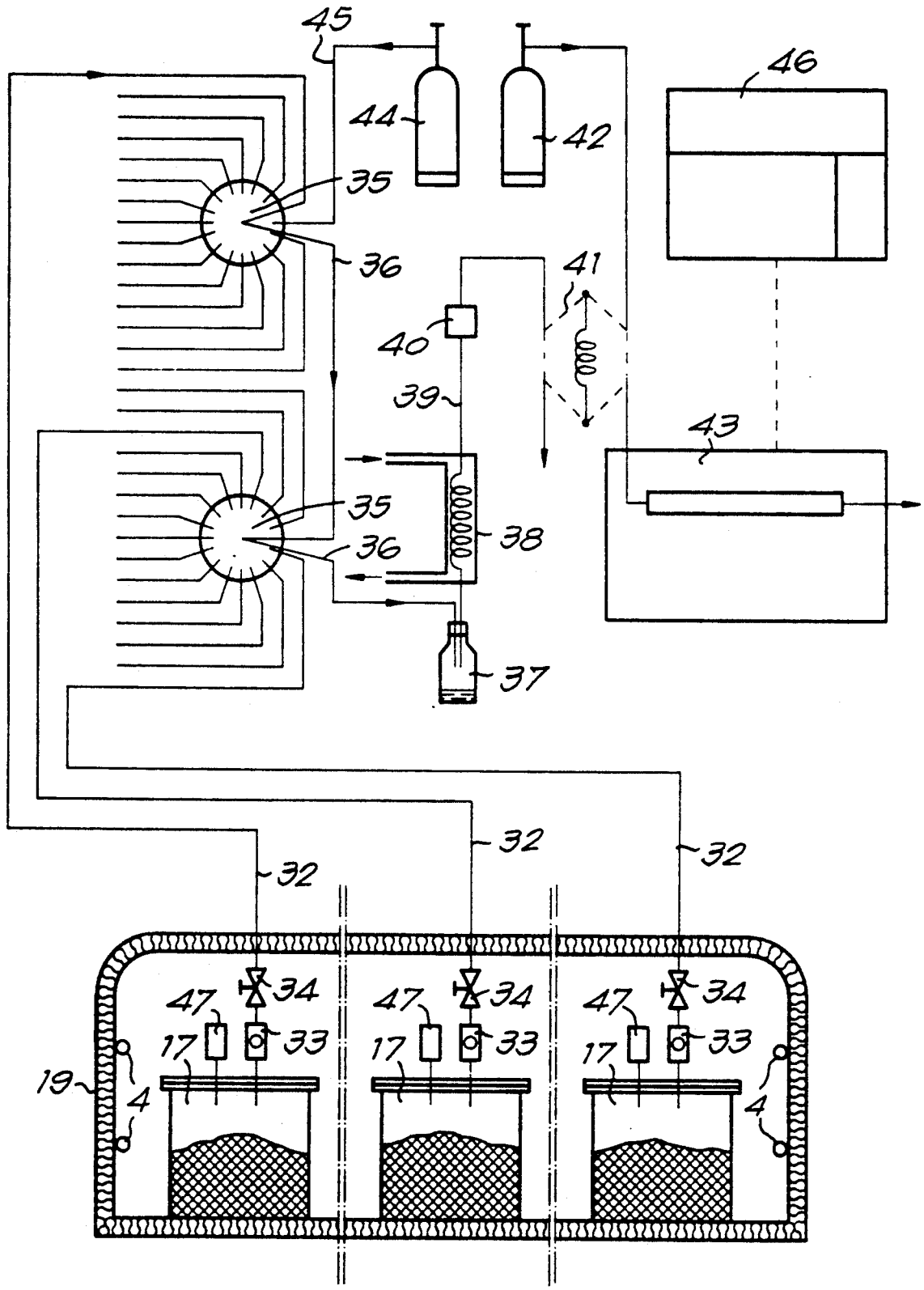
FIG. 3 shows in schematic manner and in cross-section the part of the device from FIG. 2 but in relation to another embodiment of the invention.

For this purpose use can be made of the device shown in FIG. 3. This device comprises several, for example up to thirty reactors 17, of which only three are shown, which in an incubator 19, heated by heating elements 4, are maintained at the aforementioned temperature between thirty and sixty degrees Centigrade for seven to seventy days. With this device the degradability of several products can h=determined simultaneously, which products have been mixed separately beforehand with a quantity of inoculum in the aforementioned ratios. From each mixture of inoculum-product three quantities are placed in three different reactors 17. By means of a manometer 47 the pressure is measured in each of the reactors 17. The biogas from each reactor is taken off through a pipe 32 which runs through a sample flask 33 and a valve 34 towards a multi-port valve 35. The valve 34 is opened automatically by a specific pressure in the reactor completely cut off from the air. With more than fifteen reactors 17 use is made as shown of two distribution valves 35 which are connected to each other in series since each distribution valve only has sixteen ways of which one away is connected to a source of calibration gas. This distribution valve or distribution valves 35 successively dispatch the released biogas from the various reactors via a pipe 36 towards a condensation flask 37 and a cooling device 38. In between two dispatches by the distribution valve 35 the biogas produced in a reactor is stored in this reactor. The condensation flask 37 collects the condensation moisture of the gas, possibly after cooling in the cooling device 38. The gas flows further through the pipe 39 through a very accurate flow rate meter 40 until the pressure in the reactor 17 is equal to a predetermined minimum pressure. The flow rate need not only be measured but also be integrated, since the pressure will not be constant during the release of the biogas produced.

By means of a sampling loop 41 a small amount of biogas from the pipe 39 is mixed with a carrier gas from a gas cylinder 42 and is dispatched as sample towards the gas chromatograph 43 where it is analyzed. Periodically a standard gas from a gas cylinder 44 is dispatched through the pipe 45 and the distribution valves 35 towards this gas chromatograph 43 in order to standardize it regularly internally. All results are stored in the data processor with printer 46. The volume of gas produced can be calculated from the measured flow rate development of the biogas from the various reactors and on the basis of these volumes, the degradability can be calculated as described earlier, whereby averages of volumes of carbon amounts etc. are used for each group of three identical mixtures. Gas volumes are reduced to volumes at normal conditions of temperature and pressure prior to being used with the calculations.

The invention will be specified in greater detail by the following example.

EXAMPLE

As product of which the degradability must be determined a microcrystalline cellulose powder is used for thin layer chromatography. Cellulose is generally known as a product that degrades completely of which the biodegradation starts relatively slowly. The graft is obtained from a graft fermentor which has already been fed for several weeks with the organic fraction of mixed household refuse and which reached an average gas production level of 15 ml biogas per gram dry substance in the reactor and per day. A week prior to the commencement of the experiment the graft fermentor was no longer fed in order by so doing to allow the graft to ferment out. The dry substance of the graft amounted to 30.2%. Three reactors (Erlenmeyer flasks of 2 1) were only fed with 1000 g graft. Three other reactors were fed with 1000 g graft and 18 g, this is 1.77 weight-%, cellulose powder, whereby both were very intensely mixed beforehand. After feeding the six reactors were placed in an incubator, closed and connected to the gas collecting device. Subsequently the heating was started and the reactors were incubated for 10 days at 52 degrees Centigrade.

Figure 4:
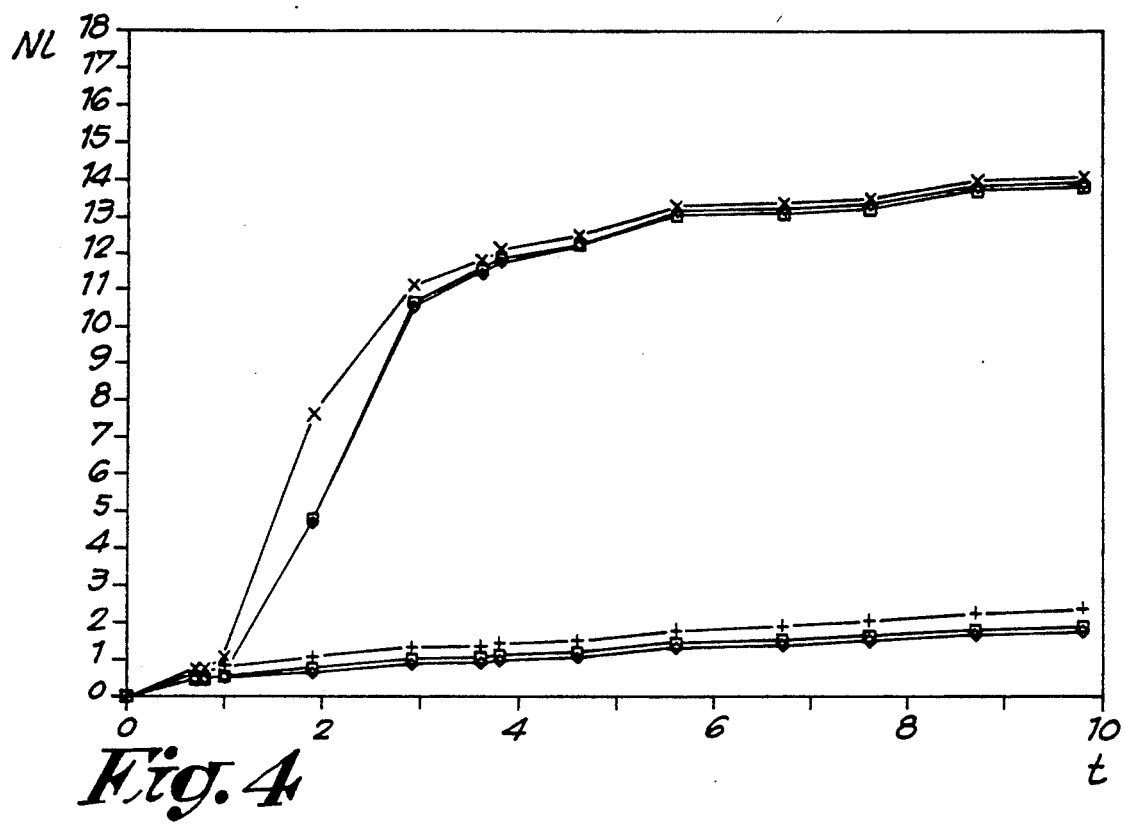
FIG. 4 shows a graph with biogas production in function of time.
Figure 5:
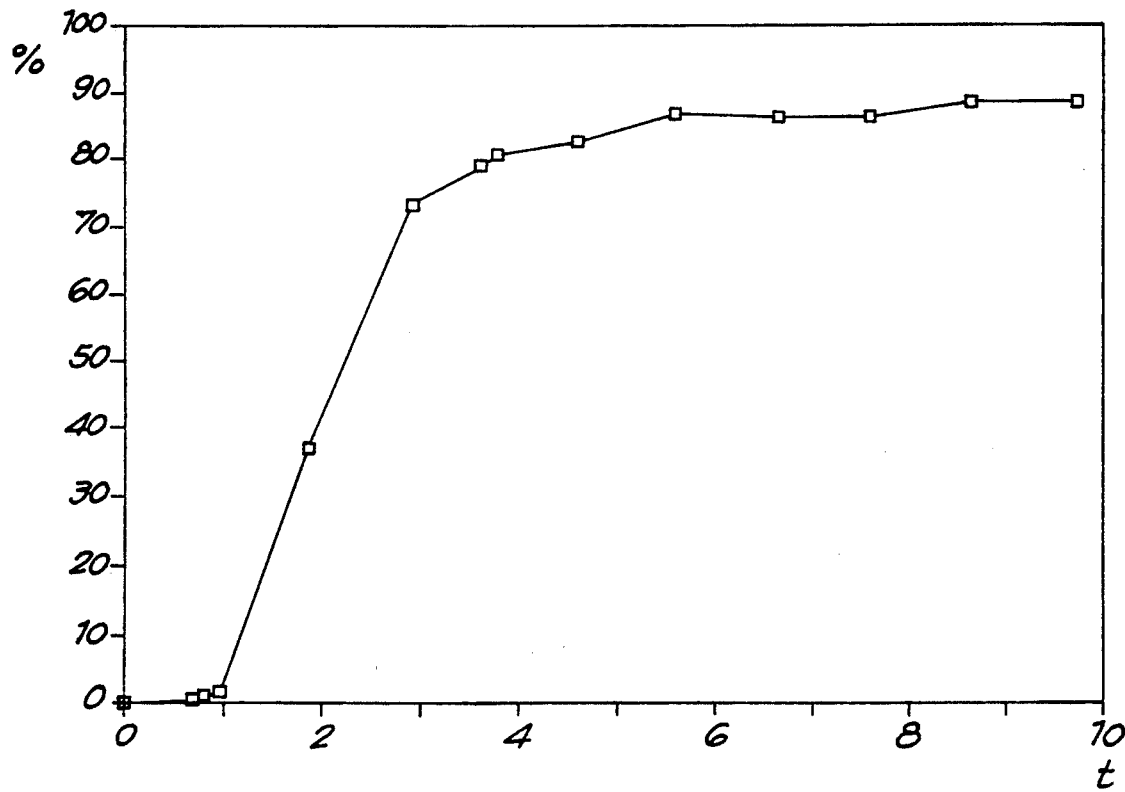
FIG. 5 shows a graph with the measured degree of degradability in function of time.

The development of the cumulative gas production is shown in FIG. 4 whereby the lower three lines give the gas production of the inoculum itself and the upper three lines show the gas production of the mixture of cellulose-inoculum. The cumulative gas production is shown in normal liters (Nl) of biogas, this is the volume of biogas in liters after conversion into standard conditions regarding temperature (0 degrees Centigrade) and pressure (1 atmosphere). After 10 days the cumulative biogas production for the graft amounted respectively to 1.88; 2.36 and 1.79 Nl; for cellulose 13.76; 13.93 and 13.87 Nl. After conversion the average net biogas production per weight unit of cellulose could be obtained. After 10 days this amounted to 648 normal milliliters of biogas per gram cellulose. The amount of biogas was converted into an amount of carbon in the form of gas while the original carbon input was also calculated with assistance of the carbon content of the cellulose used (40%). In that manner the conversion percentage of solid carbon in the product to be measured to gaseous carbon could finally be calculated. The graphic development of this percentage in function of time in days is shown in FIG. 5. The greatest part of the conversion has taken place on day two and day three of the incubation. After ten days the conversion of solid carbon originating from cellulose amounted to gaseous carbon (87%).

The present invention is in no way restricted to the embodiments described as examples and shown in the attached drawings. Such device for the determination of degradability can be implemented in various forms and dimensions without departing from the scope of the present invention.

I claim:

1. An accelerated method for determining the biodegradability of at least one product under anaerobic conditions similar to the anaerobic conditions present in a landfill, comprising the steps of:
   (a) preparing a test aliquot of a test mixture with a final dry substance content of 25 to 50% which comprises at least 80% by weight of anaerobic inoculum comprising refuse and living microorganisms and less than 20% by weight of a product, the biodegradability of which under anaerobic conditions is to be determined;
   (b) preparing a control aliquot of said anaerobic inoculum alone;
   (c) separating subjecting said test aliquot and said control aliquot of said anaerobic inoculum to a fermentation at a temperature of between 30 and 60 degrees Centigrade under anaerobic conditions for a period of time ranging from 7 to 70 days;
   (d) measuring the amount of biogas produced by said test aliquot and measuring the amount of biogas produced by said control aliquot of said anaerobic inoculum during said period of time; and
   (e) determining the biodegradability of said product during said period of time by subtracting the amount of biogas produced by said inoculum alone from the amount of biogas produced by said test mixture.

2. The method of claim 1, wherein said period of time is 7 to 10 days.

3. The method of claim 1, wherein at least two control aliquots of said anaerobic inoculum and at least two aliquots of said test mixture are subjected separately to said fermentation and the degradability of said product is determined using the average of the amounts of biogas produced by said aliquots of said inoculum and the average of the amounts of biogas produced by said aliquots of said product.

4. The method of claim 1, wherein the total amount of the degradability of at lest two products is determined, wherein said products comprise less than 20% by weight of said test mixture and said inoculum comprises at least 80% by weight of said test mixture and an equal number of aliquots of said inoculum and said test mixture are subjected to said fermentation conditions in order to determine the degradability of said products.

5. The method of claim 1, wherein the pressure and the temperature of said biogas is measured and further wherein said pressure and temperature measurements are used to convert said measured volumes of biogas produced by said anaerobic inoculum and said test mixture to volumes under standard conditions of pressure and temperature.

6. The method of claim 1, wherein the initial amount of carbon said product is determined and the biodegradability of said product is determined by calculating the ratio of the amount of gaseous carbon present in said biogas produced by said product versus the amount of initial carbon present in said product, multiplied by one hundred.

7. The method of claim 1, wherein said inoculum has produced for at least two weeks prior to use an average of at least 10 ml of biogas per gram dry substance per day.

8. The method of claim 7, wherein said inoculum has produced 20 to 30 ml of biogas per gram dry substance per day.

9. The method of claim 7, wherein said inoculum has produced at least 10 ml of biogas per gram dry substance per day for at least one month prior to use.

10. The method of claim 1, wherein said inoculum has been maintained for 7 to 14 days postfermentation without additional organic matter prior to use.

11. The method of claim 1, wherein said inoculum was prepared under dry conditions with 20 to 50% dry substance content.

12. The method of claim 1, wherein said inoculum was prepared under wet conditions and wherein the water content of said inoculum was subsequently reduced to a dry substance content of between 20 to 50%.

13. The method of claim 1, wherein the percentage by weight of said anaerobic inoculum ranges from 80-99% of said test mixture and the percentage by weight of said product ranges from 20 to 1%.

14. The method of claim 1, wherein the percentage by weight of said inoculum ranges from 80-95% of said test mixture and the percentage by weight of said product ranges from 20 to 5%.

15. The method of claim 1, in which the amount of biogas produced is measured with a gas collecting device.

16. The method of claim 1, wherein the amount of said biogas produced is determined by measuring the amount of biogas produced for a period of time which is less than said period of time ranging from 7 to 70 days and then extrapolating said measurement to estimate the amount of said biogas produced in said period of time ranging from 7 to 70 days.

17. A method according to claim 1, wherein said product is biodegradable plastic.

18. An accelerated method for determining the biodegradability of at lest one test product relative to a reference product under anaerobic conditions similar to the anaerobic conditions present in a landfill, comprising the steps of:
  (a) preparing a first aliquot of a est mixture with a final dry substance content of 25 to 50% which comprises at least 80% by weight of anaerobic inoculum comprising refuse and living microorganisms and less than 20% by weight of a test product, the biodegradability of which under anaerobic conditions is to be determined;
  (b) preparing a second aliquot of a reference mixture with a final dry substance content of 25 to 50% which comprises the same weight of anaerobic inoculum comprising refuse and living microorganisms as said first aliquot and an amount of a reference product equal to the amount of said test product in the first aliquot, the biodegradability of which under anaerobic conditions is to be determined;
  (c) preparing a control aliquot of said anaerobic inoculum alone;
  (d) separately subjecting said first, second and control aliquots to a fermentation at a temperature of between 30 and 60 degrees Centigrade under anaerobic conditions for a period of time ranging from 7 to 70 days;
  (e) measuring the amount of biogas produced by said first, second and control aliquots during said period of time; and
  (f) determining the degradability of said test product relative to said reference product during said period of time by subtracting the amount of biogas produced by said inoculum alone from the amount of biogas produced by said test mixture and by subtracting the amount of biogas produced by said inoculum alone from the amount of biogas produced by said reference mixture.

19. A process as claimed in claim 1, wherein exactly the same amount of inoculum is used in the test and control aliquots.

* * * * *